(12) United States Patent
Todd

(10) Patent No.: US 10,631,728 B2
(45) Date of Patent: Apr. 28, 2020

(54) IMAGING A RETINA OF AN EYE

(71) Applicant: UNITED KINGDOM RESEARCH AND INNOVATION, Swindon (GB)

(72) Inventor: Stephen Todd, Edinburgh (GB)

(73) Assignee: UNITED KINGDOM RESEARCH AND INNOVATION, Swindon (GB)

( * ) Notice: Subject to any disclaimer, the term of this patent is extended or adjusted under 35 U.S.C. 154(b) by 0 days.

(21) Appl. No.: 16/088,924

(22) PCT Filed: Mar. 29, 2017

(86) PCT No.: PCT/GB2017/050880
§ 371 (c)(1),
(2) Date: Sep. 27, 2018

(87) PCT Pub. No.: WO2017/168148
PCT Pub. Date: Oct. 5, 2017

(65) Prior Publication Data
US 2019/0269322 A1    Sep. 5, 2019

(30) Foreign Application Priority Data

Mar. 30, 2016 (GB) .................................. 1605355.5

(51) Int. Cl.
*A61B 3/00* (2006.01)
*A61B 3/10* (2006.01)
*A61B 3/12* (2006.01)
*A61B 3/113* (2006.01)
*A61B 3/14* (2006.01)
*A61B 3/15* (2006.01)

(52) U.S. Cl.
CPC .............. *A61B 3/12* (2013.01); *A61B 3/0008* (2013.01); *A61B 3/0091* (2013.01); *A61B 3/10* (2013.01);
(Continued)

(58) Field of Classification Search
CPC ....... A61B 3/12; A61B 3/0008; A61B 3/0016; A61B 3/0075; A61B 3/10; A61B 3/113;
(Continued)

(56) References Cited

U.S. PATENT DOCUMENTS 3,748,015 A    7/1973  Offner
4,511,227 A    4/1985  Nunokawa et al.
(Continued)

FOREIGN PATENT DOCUMENTS

CN    102641115 A      8/2012
DE      4116067 A1    11/1991
(Continued)

OTHER PUBLICATIONS

Drasdo et al., "Non-linear projection of the retinal image in a wide-angle schematic eye", British Journal of Ophthalmology (1974), vol. 58, pp. 709-714.
(Continued)

*Primary Examiner* — Jordan M Schwartz
(74) *Attorney, Agent, or Firm* — Lando & Anastasi, LLP

(57) ABSTRACT

Embodiments of the present invention provide an optical system (100) for imaging a retina through a pupil of an eye (10). The optical system (100) comprises an illumination source (120) for providing light to illuminate the eye (10) via an illumination optical system (140). The optical system further comprises an imaging device (130) for outputting image data corresponding to the retina of the eye (10) over a period of time. Said imaging device (130) is arranged to receive reflected light from the eye (10) via an imaging optical system (150). The optical system (100) further comprises a moveably mounted offner relay (110) arranged to direct light received from the illumination optical system (140) to the eye (10) and to direct reflected light from the eye
(Continued)

(10) to the imaging optical system (150). Said offner relay (110) is arranged to move to track a location of the pupil.

18 Claims, 5 Drawing Sheets

(52) U.S. Cl.
CPC ................ *A61B 3/113* (2013.01); *A61B 3/14* (2013.01); *A61B 3/152* (2013.01)

(58) Field of Classification Search
CPC ........ A61B 3/14; A61B 3/0091; G02B 17/08; G02B 17/0804
USPC .......... 351/205–206, 209, 221; 359/729–732
See application file for complete search history.

(56) References Cited

U.S. PATENT DOCUMENTS

| | | | | |
|---|---|---|---|---|
| 2007/0030450 A1* | 2/2007 | Liang | ................. | A61B 3/14 351/206 |
| 2007/0121071 A1* | 5/2007 | Jackson | ............... | A61B 3/0033 351/246 |
| 2008/0151185 A1 | 6/2008 | Saito et al. | | |
| 2011/0267615 A1* | 11/2011 | Cook | ........................ | G01J 3/02 356/326 |
| 2014/0022414 A1* | 1/2014 | Bhatia | ..................... | G01J 3/021 348/239 |
| 2014/0043460 A1* | 2/2014 | Hartell | ............... | G02B 17/0615 348/79 |
| 2016/0249803 A1* | 9/2016 | Saito | ........................ | A61B 3/12 351/221 |

FOREIGN PATENT DOCUMENTS

| | | |
|---|---|---|
| DE | 102012022967 A1 | 5/2014 |
| EP | 2460461 A1 | 6/2012 |
| WO | 2011/076943 A2 | 6/2011 |
| WO | 2013150310 A1 | 10/2013 |
| WO | 2015010133 A1 | 1/2015 |

OTHER PUBLICATIONS

International Preliminary Report on Patentability from International Application No. PCT/GB2017/050880 dated Oct. 11, 2018.

* cited by examiner

IMAGING A RETINA OF AN EYE

CROSS-REFERENCE TO RELATED APPLICATIONS

This application is a U.S. National Phase Application under 35 U.S.C. § 371 of International Application No. PCT/GB2017/050880 filed Mar. 29, 2017, which claims priority to Great Britain Application No. 1605355.5 filed Mar. 30, 2016.

BACKGROUND

It is desired to provide an image of an eye such as for monitoring a health of the eye. Age related Macular Degeneration (AMD) is a disease of the eye which causes a loss of vision. In the UK blindness and poor vision affects around 1 Million people. Providing the image of the eye is useful for determining the health of the eye.

WO 2013/150310 discloses an apparatus and method for retinal measurement. A series of images of the eye are recorded over a period of time in response to determine the eye's response to illumination. However it has been noted that it is difficult to record the image data of the eye over the period of time.

It is an object of embodiments of the invention to at least mitigate one or more of the problems of the prior art.

SUMMARY OF THE INVENTION

In accordance with aspects of the present invention, there is provided an optical system and method of providing image data as set forth in the appended claims.

In accordance with aspects of the present invention, there is provided an optical system for imaging a retina through a pupil of an eye. The optical system comprises an illumination source for providing light to illuminate the eye via an illumination optical system. The optical system further comprises an imaging device for outputting image data corresponding to the retina of the eye over a period of time. Said imaging device is arranged to receive reflected light from the eye via an imaging optical system. The optical system further comprises a moveably mounted offner relay arranged to direct light received from the illumination optical system to the eye and to direct reflected light from the eye to the imaging optical system. Said offner relay is arranged to move to track a location of the pupil. Advantageously moving said offner relay allows imaging of the retina of the eye through the pupil of the eye over the period of time in a convenient manner.

Thus, there is provided an optical system which can image a retina of an eye through a pupil of the eye over a period of time, even when the position of the pupil is not fixed.

The offner relay may comprise a primary reflector and a secondary reflector. A first portion of the primary reflector may be arranged to reflect light from the eye towards a second portion of the primary reflector via the secondary reflector. The second portion of the primary reflector may be arranged to reflect light received from the illumination optical system to the first portion of the primary reflector via the secondary reflector.

In embodiments, the primary reflector may comprise a mirrored surface. The secondary reflector may comprise a mirrored surface. The primary reflector may comprise a concave spherical mirror. The secondary reflector may comprise a convex spherical mirror.

The system may further comprise a tracking unit arranged to determine the location of the pupil. Thus, the system may determine the location of the pupil of the eye, whereby to move the offner relay to track the location of the pupil of the eye. The tracking unit may be arranged to be provided with a plurality of images of the eye, each image being from one of a plurality of different perspectives. The location of the pupil of the eye may be determined based on the plurality of images of the eye. The tracking unit may be arranged to be provided with two images of the eye each from two different perspectives at a first time point. The tracking unit may be arranged to be provided with two further images of the eye each from two different perspectives at a further time point after the first time point. Therefore, the location of the pupil of the eye may be updated based on the images of the eye at the further time point and the first time point.

The tracking unit may be further arranged to control the movement of the offner relay to track the location of the pupil. The system may further comprise a movement unit arranged to be operable to move the offner relay. The movement unit may comprise one or more servos. The tracking unit may be arranged to control the movement of the offner relay using the movement unit.

The offner relay may be arranged to move in three dimensions. Thus, even when the pupil of the eye moves in any of three dimensions, the optical system can image the retina of the eye over a period of time. In some embodiments, only the offner relay is arranged to move to track the location of the pupil.

The first portion of the primary reflector and the second portion of the primary reflector may be formed as a single reflector.

The optical system may further comprise a bleaching light source for providing light to bleach rhodopsin in a retina of the eye via the imaging optical system. The optical system may further comprise a fixation light source for providing a point for the eye to fixate on via the imaging optical system. Thus, a gaze direction of the pupil of the eye may be controlled.

The optical system may further comprise at least one separation means arranged to separate light being directed toward the offner relay from the illumination source and light being directed toward the imaging device from the offner relay. Thus, the illumination source and the imaging device need not be co-located.

Viewed from a further aspect, embodiments of the present invention provide a method of providing image data corresponding to a retina of an eye. The method comprises directing light toward the eye via an offner relay. The method further comprises receiving light reflected from the eye at the offner relay and directing the light to an imaging device. The method further comprises providing image data corresponding to the retina of the eye over a period of time. The method further comprises moving the offner relay corresponding to a location of a pupil of the eye during the period of time.

The method may further comprise determining the location of the pupil based on a plurality of images of the eye, the plurality of images of the eye being from one of a plurality of respective perspectives.

Determining the location of the pupil may comprise applying a mask to the plurality of images of the eye arranged to substantially remove bright spots in the images due to lighting reflections on the eye.

Determining the location of the pupil comprises determining a mathematical centroid of the pupil based on a known gaze direction of the eye.

It will be appreciated that embodiments of the present invention extend to computer software which, when executed by a computer, is arranged to perform any of the methods described herein. The computer software may be stored on a machine-readable storage medium. The computer software may be tangibly stored on the machine-readable storage medium.

BRIEF DESCRIPTION OF THE DRAWINGS

Embodiments of the invention will now be described by way of example only, with reference to the accompanying figures, in which.

DETAILED DESCRIPTION OF EMBODIMENTS OF THE INVENTION

Figure 1:
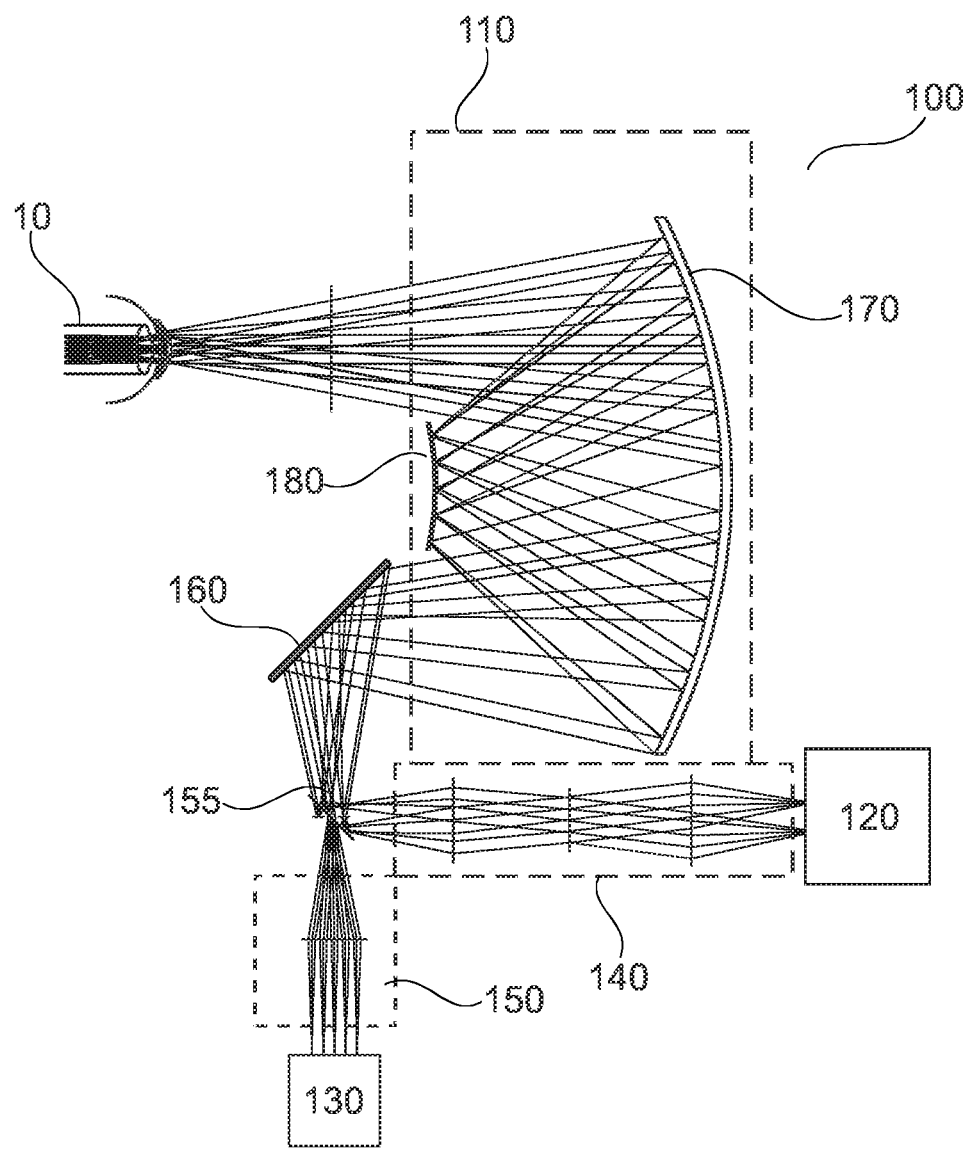
FIG. 1 schematically illustrates an optical system according to an embodiment of the invention.

FIG. 1 illustrates an optical system 100 according to an embodiment of the invention. The optical system 100 is for imaging a retina of an eye 10 through a pupil of the eye 10 of a subject over a period of time. The period of time may be, for example, at least one minute and, for example, may be for as long as thirty minutes. It will be realised, however, that other time periods may be envisaged. During such time periods the eye 10 is expected to move in location even if the subject attempts to keep the eye 10 still. For example, even if the subject's head is located upon a rest, involuntary movement of the eye 10 is likely to occur over such relatively long durations. This is in contrast to recording a single image of the eye where movement is less problematic. Embodiments of the optical system 100 comprise a moveably mounted offner relay 110 which is moved corresponding to movement of the eye 10 to at least ameliorate such problems, thereby allowing image data corresponding to the eye 10 to be provided over the period of time.

The optical system 100 comprises the offner relay 110, at least one illumination source 120 for providing light to illuminate the eye 10 and an imaging device 130 for outputting image data corresponding to at least a portion of the retina of the eye 10 over a period of time.

The optical system 100 further comprises an illumination optical system 140 and an imaging optical system 150. The illumination optical system 140 is arranged to direct light from the at least one illumination source 120 toward the eye 10 via the offner relay 110. The illumination optical system 140 is located between the at least one illumination source 120 and the offner relay 110.

The imaging optical system 150 is arranged to receive reflected light from the eye 10 and to direct the received light to the imaging device 130. The imaging optical system 150 is located between the imaging device 130 and the offner relay 110. A separation means 155 is arranged to separate light being directed toward the eye 10 and light reflected from the eye 10, as will be explained. In some embodiments the optical system 100 comprises a fold mirror 160 for directing light toward the offner relay 110 and directing reflected light received from the offner relay 110 to the separation means 155.

The at least one illumination source 120 is provided to illuminate the eye 10 whilst the imaging device 130 collects or measures received reflected illumination from at least the portion of the retina of the eye 10. In some embodiments, the portion of the retina of the eye 10 is that within a predetermined viewing field or window. The viewing field may be rectangular in shape. The viewing field may be a horizontally oriented rectangle. The viewing field may have at least a field of view of 21°. In some embodiments the field of view is 23° vertical and at least 23° horizontal, such as 30°, although it will be realised that these are merely exemplary values. The portion of the retina of the eye 10 may also be that visible through the pupil of the eye 10. The at least one illumination source 120 may comprise illumination sources of one or more predetermined wavelengths or wavelength bands. In one embodiment the at least one illumination source 120 is a broadband illumination source. However, in other embodiments the at least one illumination source 120 comprises a plurality of illumination sources of predetermined wavelengths, such that image data at each wavelength or wavelength band is output by the imaging device 130 over the predetermined period of time. For example, image data at each of a plurality of wavelengths may be output by the imaging device 130 at each of a plurality of intervals during the period of time.

The offner relay 110 forms an objective of the optical system 100. Advantageously the offner relay 110 comprises all-reflective components which avoids introduction of ghost images or specular ghost reflections which may be formed by lenses and can require use of one or more masks, such as black-spot masks, for removal. The offner relay 110 may be formed by a plurality of mirrors 170, 180, such as without any further i.e. optical or transmissive components. The offner relay 110 may comprise first and second mirrors 170, 180. The offner relay 110 in one embodiment comprises a primary mirror 170. The primary mirror 170 may be rectangular-shaped. In one embodiment the primary mirror 170 has dimensions of 110 mm by 70 mm, although it will be realised that other dimensions may be envisaged. The primary mirror 170 may be a largest mirror in the offner relay 110. The offner relay 110 further comprises a secondary mirror 180. The secondary mirror 180 is arranged to reflect illumination received from a first portion of the primary mirror 170 to a second portion of the primary mirror 170. That is, the primary mirror 170 is used in double-pass for first and third reflections whilst the secondary mirror 180 is used for a second reflection. The primary and secondary mirrors 170, 180 are spherical mirrors. The offner relay 110 reflects both light directed toward the eye 10 from the illumination source 120 and reflected light received from the eye 10 toward the imaging device 130.

The offner relay 110 is mounted upon a moving means (not shown in FIG. 1) for moving the offner relay 110. In some embodiments the moving means is arranged to move the offner relay 110 in three dimensions (x, y, z). The moving means is controlled to move the offner relay 110 to track movement of the eye 10, in particular movement of the pupil of the eye 10. In this way the imaging device 130 is able to capture images of the at least a portion of the retina through the pupil over the period of time. In some embodiments movement of the offner relay 110 is at a predetermined ratio to movement of the eye 10. For example, in one embodiment movement of the offner relay 110 of x mm results in movement of Ax mm at the pupil image. The value of A may be 2 although other values may be envisaged.

Figure 2:
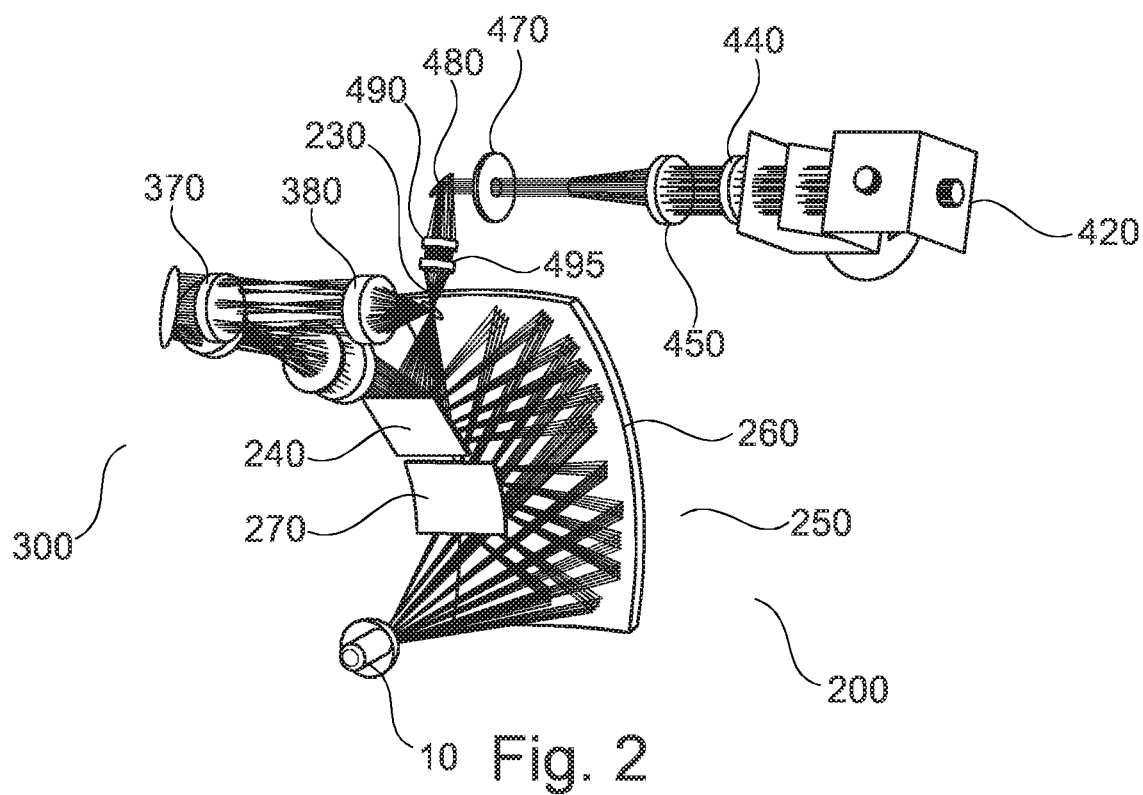
FIG. 2 shows an optical system according to another embodiment of the invention.
Figure 3:
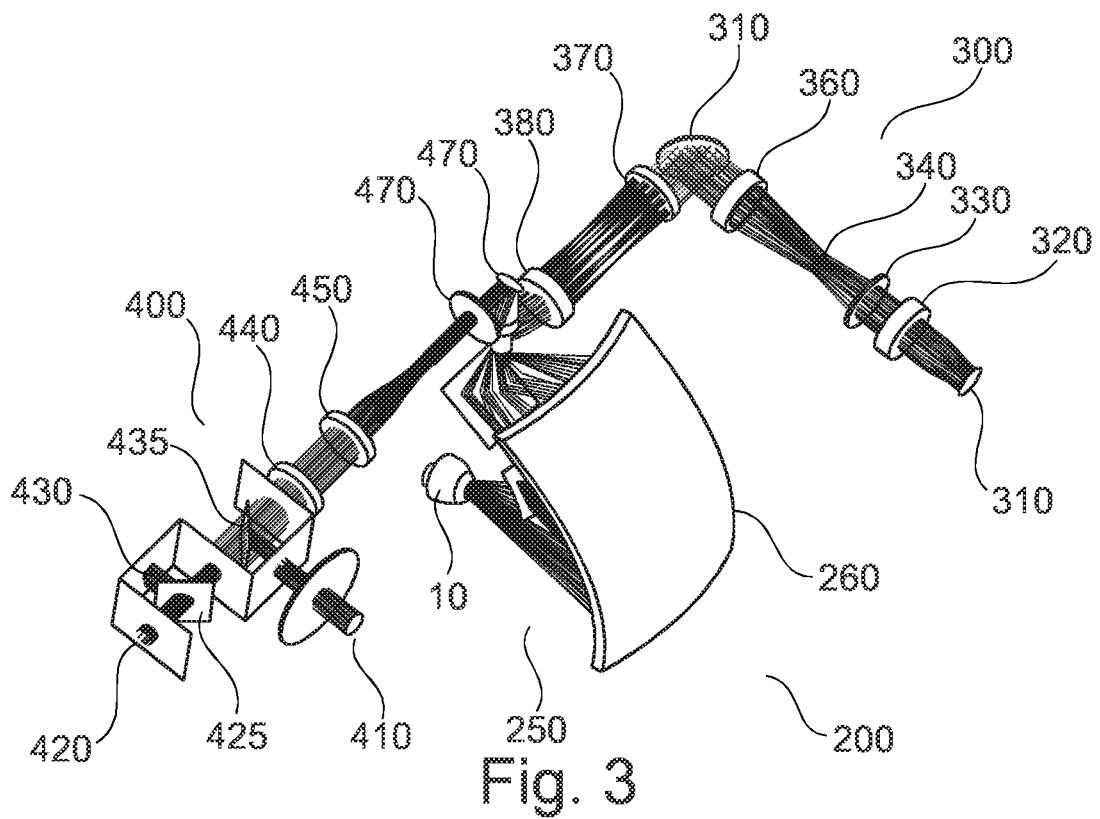
FIG. 3 shows the optical system from a different viewing angle.

FIGS. 2 and 3 illustrate an optical system 200 according to a further embodiment of the invention from different viewing angles. It will be noted that not all parts of the optical system 200 are identified with reference numerals in each figure for clarity.

As in the previously described embodiment, the optical system 200 comprises a moveable offner relay 250, an illumination optical system 300 and imaging optical system 400 as generally denoted with the respective reference numerals. The optical system 200 is for imaging a retina of an eye 10 of a subject through a pupil of the eye 10 over a period of time, as explained above. An embodiment of the illumination optical system 300 is shown schematically in FIG. 4 and an embodiment of the imaging optical system 400 is shown schematically in FIG. 5.

An illumination light source 310 is provided to illuminate the eye 10. An imaging device 410 is provided to collect or measure received reflected illumination from at least the portion of the retina of the eye 10. In addition to the previously described embodiment, the imaging optical system 400 comprises a bleaching light source 420 and a fixation target light source 430. It will be realised that one, or both, of these light sources may be included in the embodiment described above in relation to FIG. 1. The bleaching light source 420 is provided for illuminating the eye 10 to bleach rhodopsin in the retina of the eye 10. The bleaching light source 420 may be operated i.e. illuminated prior to recording images. As will be appreciated, prior to recording images of the eye 10, the bleaching light source 420 is used to illuminate the eye 10 to destroy rhodopsin in retinal cells. Such subsequently recorded images are then useful for assessing AMD. The fixation light source 430 is illuminated whilst the images of the eye are recorded during the period of time. The fixation light source 430 is visible to the subject and provides a point for the subject to focus or fixate upon, thereby assisting with maintaining a position of the pupil through which the retina is imaged.

The offner relay 250 comprises a primary mirror 260 and a secondary mirror 270. The offner relay 250 may be as described above in relation to the first embodiment of FIG. 1 and repeat description is omitted for clarity. As with the first embodiment, the offner relay 250 is moveably mounted to track movement of the eye 10 and, in particular, the pupil of the eye 10. Prior to the offner relay 250 a fold mirror 240 is provided for directing illumination to/from the offer relay 250, as previously described.

A separation means 230 is arranged to separate light being directed toward the eye 10 and light reflected from the eye 10 prior to the offner relay 250. As shown in FIGS. 2 and 3, the separation means 230 is located at an opposing side of the fold mirror 240 to the offner relay 250 i.e. upstream of the offner relay 250 for light provided from the illumination light source 310. In one embodiment the separation means is an annular mirror 230. The annular mirror 230 is located at a pupil plane 390 of the optical system 200. It will be realised that the annular mirror 230 may be used in the first described embodiment. The annular mirror 230 is provided for separating imaging and illumination optical paths. The system 200 is arranged to form an image of the subject's retina, or at least a portion thereof, at the annular mirror 230. Light to be imaged by the imaging device 130 is provided from a centre of the annular mirror 230.

Figure 4:
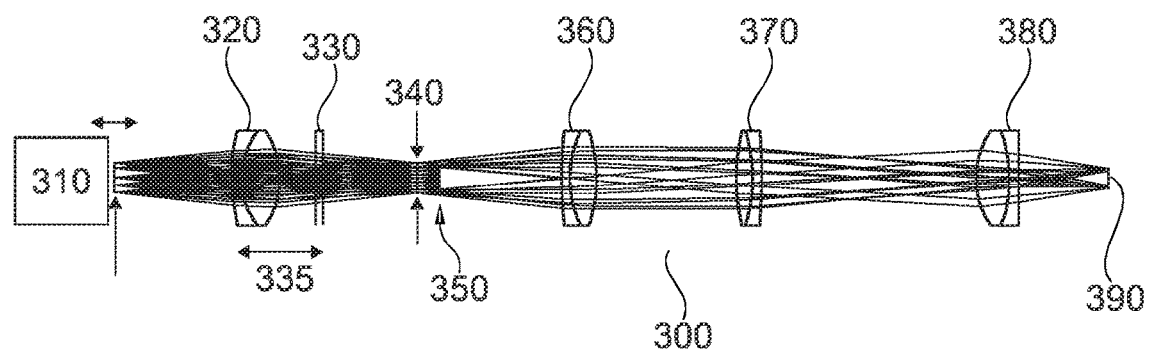
FIG. 4 shows an illumination optical system according to an embodiment of the invention.

Referring to FIG. 4, an embodiment of the illumination optical system 300 is schematically illustrated.

As previously described, the illumination light source 310 is arranged to output light at one or more predetermined wavelengths or wavelength bands. The wavelength band may be a broadband i.e. white light source or the illumination light source 310 may comprise a plurality of selectable light sources for each outputting a predetermined wavelength of light.

The illumination optical system 300 comprises a pupil mask 340 for reducing specular reflection from the cornea of the eye 10 and minimising scattered light from within the eye 10. The pupil mask 340 is relayed to the annular mirror 230. The pupil mask 340 is annular in shape.

In some embodiments the illumination optical system 300 comprises a central obscuration mask 350 located downstream of the pupil mask 340. The obscuration mask 350 is provided for reducing back-scattered light i.e. light back-scattered before reaching the eye 10. The back-scattering is reduced by separating illumination and imaging ray paths in regions where significant scattering is expected. It is expected that scattering is dominated by the crystalline lens of the eye 10. The obscuration mask 350 is arranged to reduce overlap between illumination and imaging ray paths. The obscuration mask 350 is located at a masking plane conjugate to a point near the rear of the lens of the eye 10. The obscuration mask may have a central obscuration of 3.5 mm in diameter, although it will be realised that other diameters may be envisaged.

Arranged between the pupil mask 340 and the illumination light source 310 the illumination optical system 300 comprises first and second lenses 320, 330. The first lens 320 is, in one embodiment, a doublet lens which is arranged to form a focal plane conjugate to the retina where a focal plane mask may be introduced. The focal plane mask controls which area of the retina is illuminated by defining the size of the illuminated aperture at the illumination light source 310.

The second lens 330 may be a cylindrical lens which is arranged to correct for astigmatism introduced in the image by the offner relay 250. Arranging the second lens behind the pupil mask 340 ensures that this does not degrade a relayed retinal image, which does not require astigmatism correction. By locating the pupil mask 340 at this point allows the illuminated field to be reduced to match the measurement area during optical density measurement in order to minimise stray light. Additional masks can also be introduced at the plane of the illumination light source 310 to allow measurement of the backscattered light within the eye 10. The first and second lenses 320, 330 may be moveably arranged in a focus direction 335 as illustrated in FIG. 3. A range of movement of the first and second lenses 320, 330 in the focus direction 335 may be around 8 mm to cover a required range of accommodation for refractive error of the eye (+6D to −8D).

The illumination optical system 300 may further comprise a plurality of optical components 360, 370, 380 arranged between the pupil mask 340 and the pupil plane 390 for relaying the pupil mask 340 to the pupil plane 390 at which the annular mirror 230 is located. The optical components 360, 370, 380 may have a predetermined magnification to relate a diameter of the pupil mask 230 to a diameter of the annulus of the annular mirror 230. For example, in one embodiment the annulus of the annular mirror 230 is 5 mm, the pupil mask has an outer diameter of 8 mm and the optical components 360, 370, 380 have a magnification of 0.625 to generate a retinal image of 5 mm at the annular mirror 230.

It will be realised, however, that other diameters and magnification values may be used. In one embodiment a plurality of optical components 360, 370, 380 are each doublet lenses.

Figure 5:
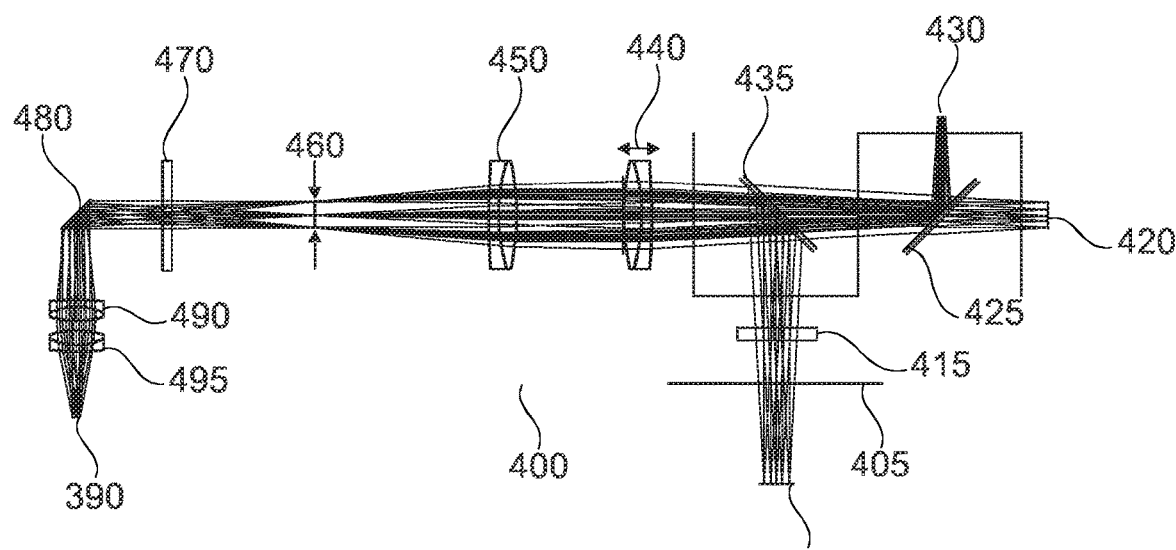
FIG. 5 shows an imaging optical system according to an embodiment of the invention.

Referring to FIG. 5, an embodiment of the imaging optical system 400 is schematically illustrated. As noted above in relation to FIGS. 2 and 3, in some embodiments the imaging optical system 400 comprises bleaching and fixation sub-systems for respectively providing bleaching functionality and a fixation point. The bleaching and fixation sub-systems comprise the bleaching light source 420 and the fixation target light source 430. The fixation target light source 430 may be arranged to output light having a wavelength of around 450 nm i.e. the fixation target light source 430 may be blue in colour.

The imaging optical system 400 receives light from the centre of the annular mirror 230 at the output of the offner relay 250 and forms a focused image at an imaging plane at which the imaging device 410 is located. Advantageously the imaging optical system 400 uses the same optical components to relay light from the bleaching light source 420 and the fixation target light source 430 to the retina at the annular mirror 230, thereby allowing a single focusing mechanism to be used to adjust for the refractive error in the eye 10, simultaneously focusing the focal planes of the imaging device 410, the bleaching light source 420 and the fixation target light source 430 onto the retina of the eye 10.

The imaging optical system 400 comprises a first beamsplitter 425 for combining light from the bleaching and fixation sub-systems, in particular light emitted from the bleaching light source 420 and the fixation target light source 430. A shutter 405 may be provided in relation to the imaging device 410. The shutter 405 is operable responsive to activation of the bleaching light source 420 to prevent bleaching light reaching the imaging device 410. A filter 415 may also be provided in relation to the imaging device 410 for filtering fixation light from the fixation target light source 430 from reaching the imaging device 410. The beamsplitter 425 may be a dichroic beamsplitter.

A second beamsplitter 435 is arranged to separate an optical path from the first beamsplitter 425 and the imaging device 410. The second beamsplitter is, in some embodiments, a broadband beamsplitter plate with high reflectivity.

The imaging optical system 400 comprises magnifying optical components 490, 495 for magnifying the retinal image at the pupil plane 390 of the optical system 200. The magnifying optical components 490, 495 in some embodiments comprise first and second lenses 490, 495. The magnifying optical components are located adjacent the pupil plane 390. A magnification of the magnifying optical components 490, 495 may be 4× although it will be realised that other magnifications may be envisaged. A pupil mask may be included in the imaging optical system 400 associated with the magnifying optical components 490, 495.

A cylindrical lens 470 may be arranged downstream i.e. in the direction of the imaging device 410 of the imaging optical system 400. The cylindrical lens is provided for compensating for the astigmatism of the offner relay 250. The cylindrical lens may have a focal length of around 1 m although it will be realised that other focal length lenses may be used.

The imaging optical system 400 further comprises a pupil stop 460 in the form of a mask. The pupil stop is arranged downstream of the lens 470 at an intermediate pupil plane. The input pupil imaging optical system 400 is roughly defined by the annular mirror 230 at an input to the imaging path. However the pupil is defined by a mask at this intermediate pupil plane. The pupil at this plane is magnified by a factor of 4.0, as described above by the magnifying optical components 490, 495. Therefore a mask having an aperture of 6 mm diameter may be used to define a circular input pupil of diameter 1.5 mm at the eye itself (and at the annular mirror plane).

The imaging optical system 400 further comprises, in some embodiments, one or more lenses 440, 450 arranged between the pupil stop 460 and the second beamsplitter 435. In the embodiment shown in FIG. 5 the imaging optical system 400 comprises lenses 440, 450 arranged to form an image of the retina of the eye 10 at the output focal planes (the planes of the imaging device 410, the fixation target light source 430 and the bleaching light source 420). The lens 440 is moveably mounted for focussing the image. In one embodiment the lens 440 is moveable over a total range of 3 mm to accommodate a range of refractive errors of the eye of +6D to −8D.

Figure 6:
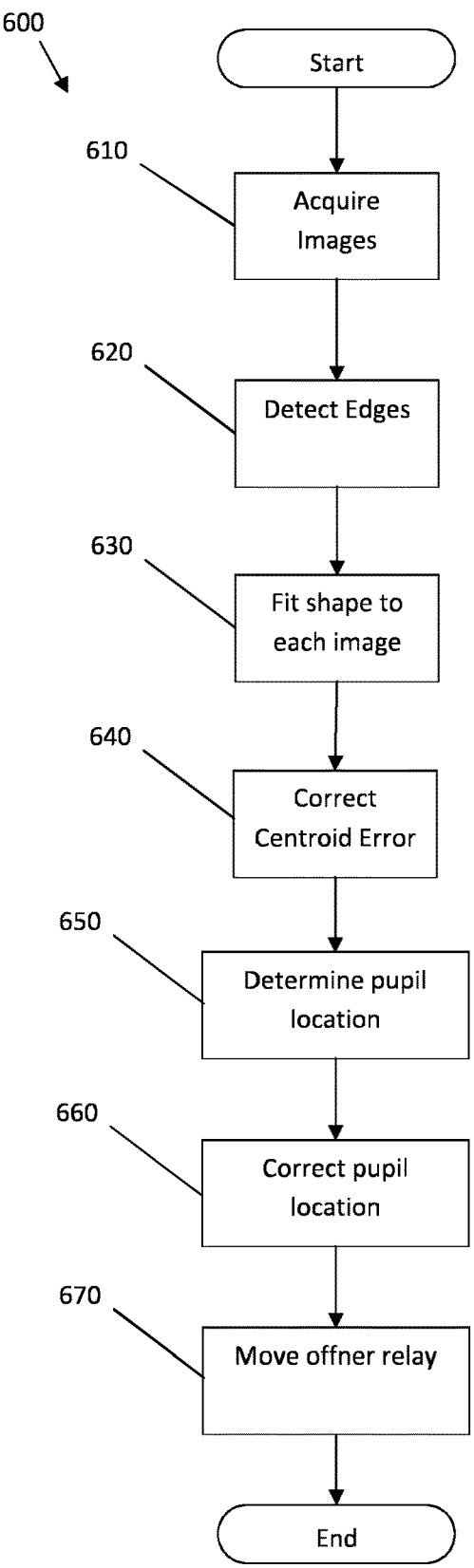
FIG. 6 illustrates a method of determining the location of the pupil of the eye according to an embodiment of the invention.

FIG. 6 illustrates a method 600 of determining the location of the pupil of the eye according to an embodiment of the invention. The method 600 of determining the location of the pupil of the eye comprises an image acquisition step 610 to acquire images of the eye from at least two different perspectives. In embodiments, the image acquisition step 610 comprises acquiring images of the eye from two cameras mounted at different locations on one or more portions of the optical system 100 at a given point in time. In this way, the eye is viewed from two different perspectives at the given point in time. New images from each camera may be acquired at a later point in time. Therefore, a plurality of sets of images may be recorded over a period of time.

The method 600 further comprises an edge detection step 620. During the edge detection step 620, one or more edge detection techniques are used to detect one or more edges in each of the two received images. The one or more edges may correspond to known features of the eye, such as an edge of the pupil.

The method 600 further comprises an shape-fitting step 630. During the ellipse-fitting step 630, a predetermined shape is fitted to the one or more edges detected during the edge detection step 620. The predetermined shape may be, in some embodiments, an ellipse although it will be appreciated that other shapes may be used. Advantageously the use of an ellipse best-fits the pupil.

In embodiments, the shape-fitting step 630 comprises using a random sample consensus algorithm (RANSAC) to fit the ellipse to the edge data. In some embodiments, a mask may be applied in the RANSAC algorithm to discard parts of the ellipse likely to contain outliers. For example, the mask can be used to discard parts of the ellipse containing bright spots due to lighting reflections on the eye. Once fitted, the outline of the ellipse substantially corresponds to the edge of a feature in the image of the eye, such as the pupil.

The method 600 further comprises a centroid error correction step 640. During the centroid error correction step, an error between the centre of the shape, such as the ellipse, and the centre of the pupil is corrected. The error may arise because the eye is viewed at an angle. The correction to apply is determined in embodiments of the invention based on a known gaze direction and a location and optical properties of the cameras used to acquire the images of the eye. The centroid error correction step 640 may comprise obtaining a pre-determined correction to apply to a determined centroid position of the pupil from a data store, such as a lookup table stored in memory, although it will be appreciated that other data storage structures may be used. In this way, the correction to apply is predetermined for a number of different ellipse centroid locations in the acquired images. Thus the correction is associated with the particular location of the eye within the image.

The method 600 further comprises a pupil location determination step 650. During the pupil location determination step 650, the location in three dimensions (x, y z) (3D location) of the pupil is determined. In some embodiments the location is determined based on an intersection between lines travelling from the two cameras used for the image acquisition step 610 towards the corrected centroid location determined in centroid error correction step 640. The corrected centroid location is the centroid location of the pupil in each image. It will be appreciated that if the 2D location of the centroid of the pupil is correctly determined in each image, and the location of the cameras from which the images have been acquired is known, then the 3D location of the pupil can be determined.

In embodiments, the method 600 further comprises a pupil location correction step 660. During the pupil location correction step 660, a further correction to the pupil location determined in the pupil location determination step 650 is applied. The further correction may be required due to errors in the location of the cameras used to determine the pupil location during the pupil location determination step 650. The further correction may be read from a further data store, such as a second lookup table stored in memory. The second lookup table may be created or optimised from default value(s) during a calibration stage, which may be performed during a setup of the apparatus. In this way, the method 600 uses images of the pupil of the eye acquired from different locations to determine the 3D location of the pupil of the eye.

The method 600 further comprises an offner relay movement step 670. During the offner relay movement step 670, the position of the offner relay 110 is changed based on at least the determined 3D location of the pupil of the eye. In some embodiments, the offner relay movement step 670 comprises transmitting one or more motor control signals to motors connected to the offner relay 110 to move the offner relay 110. The motors may form one or more servos arranged to control the location of the offner relay 110.

It will be appreciated that the method 600 may be a periodically repeated process, whereby the location of the pupil of the eye is periodically updated. In this way, the determined location of the pupil of the eye may be used to control the location of the offner relay 110 to track the pupil of the eye over the period of time, thereby ensuring that the image of the retina of the eye through the pupil of the eye is provided at the imaging device 130.

Figure 7:
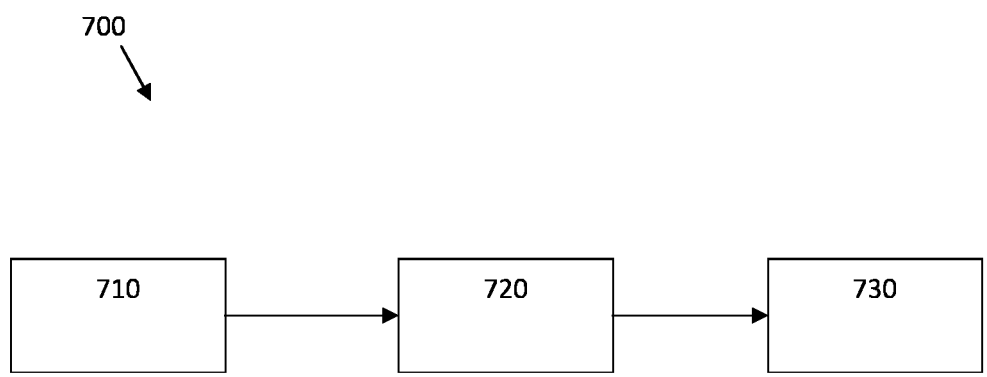
FIG. 7 illustrates an eye tracking system according to an embodiment of the invention.

FIG. 7 illustrates an eye tracking system 700 according to an embodiment of the invention. The eye tracking system 700 is configured to carry out the steps of the method 600 described previously with reference to FIG. 6. The eye tracking system comprises an image acquisition system 710 for acquiring images of the eye from at least two different perspectives. In embodiments, the image acquisition system 710 comprises two cameras mounted at different locations on one or more portions of the optical system 100. Each camera is configured to capture an image of the eye.

The eye tracking system 700 further comprises a pupil location determination module 720. The pupil location determination module 720 is configured to carry out the edge detection step 620, the ellipse-fitting step 630, the centroid error correction step 640, the pupil location determination step 650 and the pupil location correction step 660 of the method 600 described in relation to FIG. 6. In particular, the pupil location determination module 720 is configured to receive images captured by the image acquisition system 710 and to determine the location of the pupil of the eye based on the received images. In embodiments, the pupil location determination module 720 receives two images of the eye from two different perspectives, and comprises a memory and one or more processors. The memory includes instructions which, when executed by the one or more processors, cause the pupil location determination module 720 to determine the location of the pupil of the eye based on the two received images using the method as described in relation to FIG. 6 previously.

The eye tracking system 700 further comprises a motor controller 730 for controlling a motor connected to the offner relay 110, whereby to move the offner relay 110 based on the determined 3D location of the pupil of the eye in accordance with the offner relay movement step 670 of method 600 described in relation to FIG. 6 previously. In embodiments, the movement to apply to the offner relay 110 may be determined based on both the determined 3D location of the pupil and a previous 3D location of the pupil. In embodiments, the motor controller 730 receives a control signal from the pupil location determination module 720 configured to cause the motor connected to the offner relay 110 to move the offner relay a preset amount in an x direction, a y direction and a z direction. The x, y and z directions are mutually orthogonal directions.

In summary, there is provided an optical system (100) for imaging a retina through a pupil of an eye (10). The optical system (100) comprises an illumination source (120) for providing light to illuminate the eye (10) via an illumination optical system (140). The optical system further comprises an imaging device (130) for outputting image data corresponding to the retina of the eye (10) over a period of time. Said imaging device (130) is arranged to receive reflected light from the eye (10) via an imaging optical system (150). The optical system (100) further comprises a moveably mounted offner relay (110) arranged to direct light received from the illumination optical system (140) to the eye (10) and to direct reflected light from the eye (10) to the imaging optical system (150). Said offner relay (110) is arranged to move to track a location of the pupil.

It will be appreciated that embodiments of the present invention can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are embodiments of machine-readable storage that are suitable for storing a program or programs that, when executed, implement embodiments of the present invention. Accordingly, embodiments provide a program comprising code for implementing a system or method as claimed in any preceding claim and a machine readable storage storing such a program. Still further, embodiments of the present invention may be conveyed electronically via any medium such as a communication signal carried over a wired or wireless connection and embodiments suitably encompass the same.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. An optical system for imaging a retina through a pupil of an eye, comprising:
   an illumination source for providing light to illuminate the eye via an illumination optical system;
   an imaging device for outputting image data corresponding to the retina of the eye over a period of time, wherein said imaging device is arranged to receive reflected light from the eye via an imaging optical system; and
   a tracking unit arranged to determine the location of the pupil;
   a moveably mounted offner relay arranged to direct light received from the illumination optical system to the eye and to direct reflected light from the eye to the imaging optical system;
   wherein said tracking unit is arranged to control the movement of the offner relay based on the location of the pupil.

2. The system of claim 1, wherein the offner relay comprises a primary reflector and a secondary reflector, wherein a first portion of the primary reflector is arranged to reflect light from the eye towards a second portion of the primary reflector via the secondary reflector, and wherein the second portion of the primary reflector is arranged to reflect light received from the illumination optical system to the first portion of the primary reflector via the secondary reflector.

3. The system of claim 1, wherein a primary reflector of the offner relay comprises a concave spherical mirror, and wherein a secondary reflector of the offner relay comprises a convex spherical mirror.

4. The system of claim 1, wherein the offner relay is arranged to move in three dimensions.

5. The system of claim 1, wherein the tracking unit comprises a plurality of cameras arranged to provided a plurality of differing imaging perspectives, wherein the plurality of images from the tracking unit include at least two images from the differing image perspectives.

6. The system of claim 1, further comprising a movement unit arranged to be operable to move the offner relay.

7. The system of claim 6, wherein the movement unit comprises one or more servos.

8. The system of claim 2, wherein the first portion of the primary reflector and the second portion of the primary reflector are formed as a single reflector.

9. The system of claim 1, further comprising, in addition to the illumination light source, a bleaching light source arranged within the system to provide light to bleach rhodopsin in a retina of the eye via the imaging optical system.

10. The system of claim 1, further comprising, in addition to the illumination light source, a fixation light source arranged within the system for providing a point for the eye to fixate on via the imaging optical system.

11. The system of claim 1, further comprising at least one separation means arranged to separate light being directed toward the offner relay from the illumination source and light being directed toward the imaging device from the offner relay.

12. A method of providing image data corresponding to a retina of an eye, comprising
   directing light toward the eye via an offner relay;
   receiving light reflected from the eye at the offner relay and directing the light to an imaging device;
   tracking to determine a location of a pupil of the eye;
   providing image data corresponding to the retina of the eye over a period of time; and
   moving the offner relay corresponding to the tracked location of the pupil of the eye during the period of time.

13. The method as claimed in claim 12, further comprising determining the location of the pupil based on a plurality of images of the eye, wherein the plurality of images include at least two images from differing image perspectives.

14. The method as claimed in claim 13, wherein determining the location of the pupil comprises applying a mask to the plurality of images of the eye arranged to substantially remove bright spots in the images due to lighting reflections on the eye.

15. The method as claimed in claim 13, wherein determining the location of the pupil comprises determining a mathematical centroid of the pupil based on a known gaze direction of the eye.

16. Computer software tangibly stored on a machine-readable storage medium which, when executed by a computer is arranged to perform a method according to claim 12.

17. The system of claim 1, wherein said offner relay is arranged to move in its entirety relative to the imaging device.

18. The method as claimed in claim 12, further comprising moving the offner relay in its entirety relative to the imaging device.

* * * * *

UNITED STATES PATENT AND TRADEMARK OFFICE
CERTIFICATE OF CORRECTION

PATENT NO.         : 10,631,728 B2
APPLICATION NO.    : 16/088924
DATED              : April 28, 2020
INVENTOR(S)        : Stephen Todd Page 1 of 1

It is certified that error appears in the above-identified patent and that said Letters Patent is hereby corrected as shown below:

In the Claims

Column 11, Claim 5, Line 55, delete "provided" and insert -- provide --.

Signed and Sealed this
Second Day of June, 2020

Andrei Iancu
*Director of the United States Patent and Trademark Office*